(12) United States Patent
Happonen et al.

(10) Patent No.: US 7,122,037 B2
(45) Date of Patent: Oct. 17, 2006

(54) BONE FRACTURE FASTENER AND MATERIAL FOR PRODUCTION THEREOF

(75) Inventors: Harri Happonen, Tampere (FI); Timo Pohjonen, Tampere (FI); Auvo Kaikkonen, Tampere (FI); Jan Nieuwenhuis, Gorinchem (NL)

(73) Assignee: Inion Ltd., Tampere (FI)

( * ) Notice: Subject to any disclaimer, the term of this patent is extended or adjusted under 35 U.S.C. 154(b) by 45 days.

(21) Appl. No.: 09/859,974

(22) Filed: May 17, 2001

(65) Prior Publication Data

US 2002/0177851 A1    Nov. 28, 2002

(51) Int. Cl.
    *A61B 17/58* (2006.01)
(52) U.S. Cl. .......................................... 606/73; 606/77
(58) Field of Classification Search ................. 606/60, 606/62, 65, 67, 72, 73; 424/426, 423
    See application file for complete search history.

(56) References Cited

U.S. PATENT DOCUMENTS

| | | | | |
|---|---|---|---|---|
| 4,142,293 A | | 3/1979 | Tieche ........................... 32/15 |
| 4,338,926 A | * | 7/1982 | Kummer et al. .............. 606/70 |
| 4,776,329 A | | 10/1988 | Treharne ............... 128/92 YR |
| 4,905,679 A | | 3/1990 | Morgan ........................ 606/70 |
| 4,959,064 A | * | 9/1990 | Engelhardt ................... 606/65 |
| 4,973,333 A | | 11/1990 | Treharne ...................... 606/77 |
| 5,108,399 A | | 4/1992 | Eitenmuller et al. .......... 606/77 |
| 5,116,337 A | * | 5/1992 | Johnson ....................... 606/73 |
| 5,275,601 A | * | 1/1994 | Gogolewski et al. ......... 606/72 |
| 5,423,858 A | | 6/1995 | Bolanos et al. ............. 606/220 |
| 5,470,334 A | * | 11/1995 | Ross et al. ................... 606/72 |
| 5,549,677 A | * | 8/1996 | Durr et al. ............... 623/16.11 |
| 5,569,250 A | | 10/1996 | Sarver et al. ................. 606/69 |
| 5,601,429 A | | 2/1997 | Blacklock ................... 433/174 |
| 5,601,553 A | | 2/1997 | Trebing et al. ............... 606/61 |
| 5,641,501 A | * | 6/1997 | Cooper et al. .............. 424/426 |
| 5,658,312 A | | 8/1997 | Green et al. ................. 606/219 |
| 5,713,920 A | * | 2/1998 | Bezwada et al. ........... 606/230 |
| 5,743,914 A | * | 4/1998 | Skiba .......................... 606/73 |
| 5,868,749 A | | 2/1999 | Reed ........................... 606/76 |
| 5,935,127 A | * | 8/1999 | Border ........................ 606/62 |
| 5,968,047 A | * | 10/1999 | Reed ........................... 606/76 |
| 6,130,271 A | | 10/2000 | Jarrett et al. ................ 523/113 |
| 6,235,869 B1 | | 5/2001 | Roby et al. ................. 528/354 |

(Continued)

FOREIGN PATENT DOCUMENTS

EP        0 585 476        3/1994

(Continued)

OTHER PUBLICATIONS

R. Suuronen, P. Lane, E. Sarkiala, T. Pohjonen, and C. Lindqvist: *Sagittal split osteotomy fixed with biodegradable, self-reinforced poly-L-lactide screws, A pilot study in sheep*. Int. J. Oral Maxillofac. Surg. 1992:21:303-308.

(Continued)

*Primary Examiner*—Sharon Kennedy
(74) *Attorney, Agent, or Firm*—Banner & Witcoff, Ltd.

(57) ABSTRACT

A fastener for the treatment of fractures and the materials for production thereof. The fastener having a head with a contact portion for an installation tool and an attaching part having a treaded portion. The threads of the threaded portion are 5 to 20 % of the height of the outer diameter of the thread. The material for producing the fastener is a blend containing a biodegradable base material and one or more copolymer additives so that at room temperature the ductility of the blend is substantially higher than that of the pure base material. The base material may be a biodegradable polymer and/or a copolymer.

13 Claims, 3 Drawing Sheets

U.S. PATENT DOCUMENTS

Figure 1:
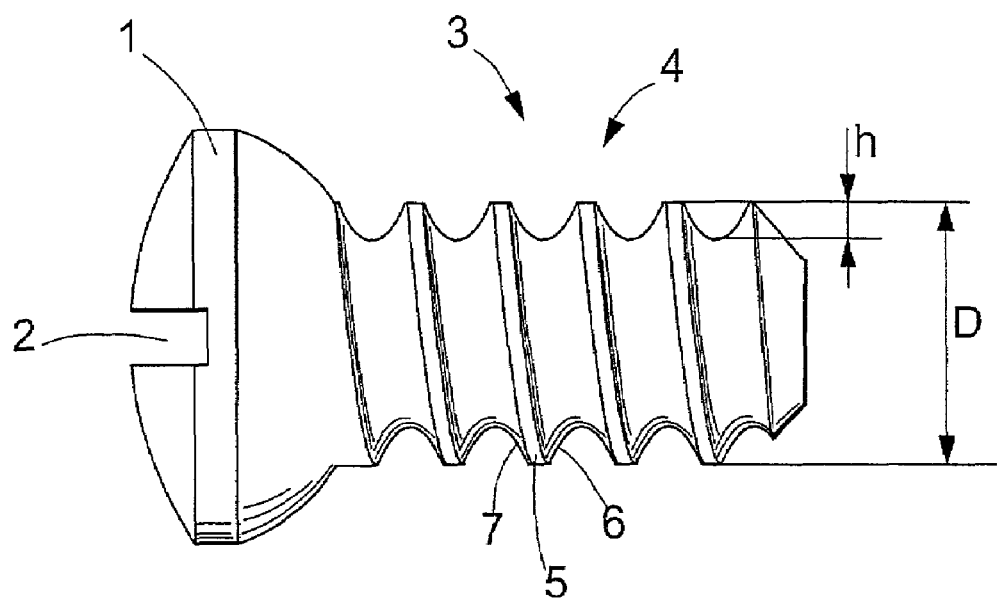

| | | | |
|---|---|---|---|
| 6,241,732 B1* | 6/2001 | Overaker et al. | 606/72 |
| 6,269,716 B1 | 8/2001 | Amis | 81/121.1 |
| 6,343,531 B1 | 2/2002 | Amis | 81/121.1 |
| 6,477,923 B1 | 11/2002 | Amis | 81/121.1 |
| 6,547,561 B1* | 4/2003 | Meller et al. | 433/80 |
| 6,863,671 B1* | 3/2005 | Strobel et al | 606/73 |
| 2002/0022843 A1* | 2/2002 | Michelson | 606/70 |
| 2002/0123751 A1* | 9/2002 | Fallin | 606/73 |

FOREIGN PATENT DOCUMENTS

| | | | |
|---|---|---|---|
| WO | WO 89/01767 | | 3/1989 |
| WO | WO 94/11441 | * | 5/1994 |
| WO | WO 94/27506 | | 12/1994 |
| WO | WO 01/22894 | | 4/2001 |

OTHER PUBLICATIONS

E. Partio, O. Bostman, E. Hirvensalo, S. Vainionpaa, K. Vihtonen, H. Patiala, P. Tormala, and P. Rokkanen: *Self-Reinforced Absorable Screws in the Fixation of Displaced Ankle Fractures: A Prospective Clinical Study of 152 Patients*. Journal of Orthopaedic Trauma, vol. 6, No. 2, pp. 209-215.

International Standard, ISO 5835 First Edition Jan. 15, 1991 *Implants for surgery-Metal bone screws with hexagonal drive connection, spherical under-surface of head, asymmetrical thread-Dimensions*.

H. Peltoniemi, R. Tulamo, H. Pihlajamaki, M. Kallioinen, T. Pohjonen, P. Tormala, P. Rokkanen, and T. Waris: *The Healing of Cranial Osteomy Lines Fixed with SR-PLLA Plates and Titanium Screws: an Experimental Study in Growings Sheep*, Transactions of the 11th Congress of the International Confederation of Plastic, Reconstructive and Aesthetic Surgery, P. 630, Yokohama, Japan, Apr. 16-21, 1995.

B. Eppley and A.M. Sadove: *A Comparison of Resorable and Metallic Fixation in Healing of Calvarial Bone Grafts*, Plastic and Reconstructive Surgery, vol. 96, No.2 Aug. 1995.

* cited by examiner

BONE FRACTURE FASTENER AND MATERIAL FOR PRODUCTION THEREOF

The invention relates to a fastening means for treatment of fractures, the fastening means comprising a head, which is provided with a contact portion for an installation tool, and an attaching part, which comprises a screw thread.

The invention further relates to a material for producing a fastening means intended for treatment of fractures, the material being a blend which comprises a base material, which is biodegradable polymer and/or copolymer.

Screws and tacks which are made of materials that dissolve in the body, i.e. biodegradable materials, and used for treatment of fractures are known. These fastening means are typically used for attaching bars and plates to the bone, which support the bone as the fracture heals. The implant keeps the bone in the right position so that it can heal as well as possible. When the fastening means and the implant are made of materials which dissolve in the body, they do not need to be removed, and thus a removal operation after the bone has healed can be avoided. This is naturally advantageous in respect of patient satisfaction, resources and costs.

Implants are fixed by fitting the fastening means through the holes provided in the implant and by attaching the fastening means to a mounting hole drilled in the bone. Screws are fixed by twisting screw threads into the corresponding threads in the mounting hole. Tacks are fastened by pressing them into the mounting hole, usually by shooting.

In some applications the screw is a better fastening means, in others it is more advantageous to use a tack. The producers of fastening means consequently have a large variety of different screws and tacks available in different sizes. The fact that the shape of a screw differs substantially from that of a tack and they are used differently causes a number of problems. First of all, screws and tacks have to be manufactured on different production lines by different tools. Secondly, the hospital personnel or any other party who performs the operation has to manage a large number of different items of fastening means. Management usually includes several phases, e.g. ordering of items, storage, supply to the actual operation, other handling, etc. Thirdly, a considerable number of instruments, e.g. containers, are needed for different fastening means in the operating space, e.g. in an operating room. All the above-mentioned issues cause costs and troubles of various kinds: production costs arising from different tools, production lines and the need for space; logistics costs in hospitals; lack of space in the operating room and complexity due to the large number of instruments.

The object of the present invention is to provide a new improved fastening means for treatment of fractures and material for the production of said fastening means.

The fastening means of the invention is characterized in that the attaching part of the fastening means can be fixed in a mounting hole in two different ways: like a screw or a tack.

The material of the invention is characterized in that in addition to the base material the blend contains a copolymer additive so that at room temperature the ductility of the blend is substantially higher than that of pure base material.

The basic idea of the invention is that the fastening means can be fixed in the mounting hole both by twisting the threads of the fastening means into the threads of the mounting hole and by pressing the attaching part of the fastening means into the mounting hole. Furthermore, the idea of a preferred embodiment of the invention is that the head is provided with an attaching part which fastens an installation tool detachably to the fastening means. The basic idea related to the material for producing the fastening means is that the material is a blend which contains a base material and one or more copolymer additives, which comprise one or more monomers, the ductility of the blend being higher at room temperature than that of pure base material. Furthermore, the idea of a preferred embodiment of the material according to the invention is that the copolymer additive contains trimethylene carbonate (TMC) or dioxanone. The basic idea of a second preferred embodiment of the material according to the invention is that the base material contains polylactide, polyglycolide, poly(L-lactide), poly(D-lactide), poly(L-lactide-co-D,L-lactide), poly(L-lactide-co-mesolactide), poly(L-lactide-co-glycolide), poly(L-lactide-co-$\epsilon$-caprolactone), poly(D,L-lactide-co-mesolactide), poly(D,L-lactide-co-glycolide), poly(D,L-lactide-co-$\epsilon$-caprolactone), poly(mesolactide-co-glycolide) and/or poly(mesolactide-co-$\epsilon$-caprolactone). The basic idea of a third embodiment of the material according to the invention is that the share of copolymer additive in the blend is 1 to 50% by weight, preferably 20 to 50% by weight and most preferably 20 to 40% by weight.

An advantage of the invention is that the fastening means replaces the screw and the tack and thus it can be flexibly applied in various fastening tasks that arise in treatment of fractures. The fastening means simplifies the manufacturing phase because only one kind of fastening means needs to be manufactured. Consequently, the production costs will be lower than previously. The fastening means according to the invention reduces the number of items that need to be managed, which also reduces the costs and simplifies the logistics related to fastening means. The number of instruments needed in the operating room decreases, which simplifies and facilitates the work of the surgeons and other persons participating in the operation. An advantage of the material for producing the fastening means according to the invention is that the material is ductile at room temperature. Thanks to this, the probability that the fastening means breaks when attached by shooting is very low.

Figure 2:
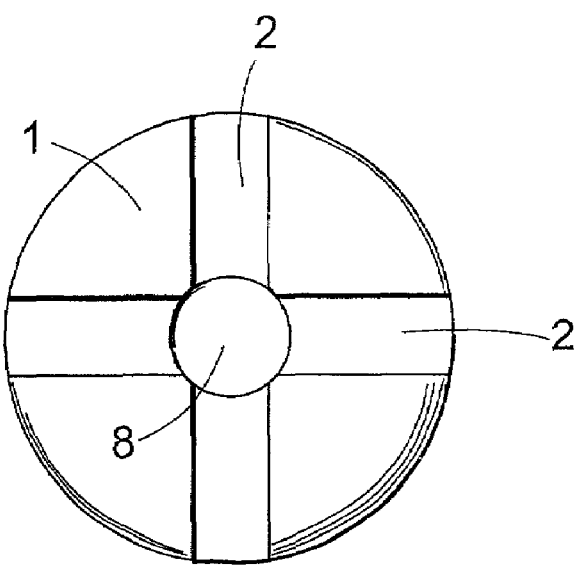
Figure 3:
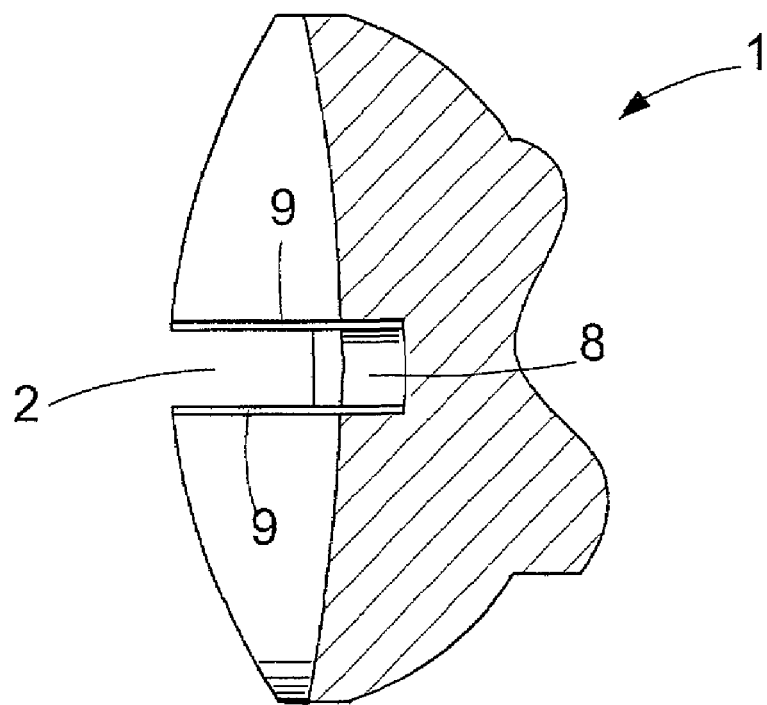
Figure 4:
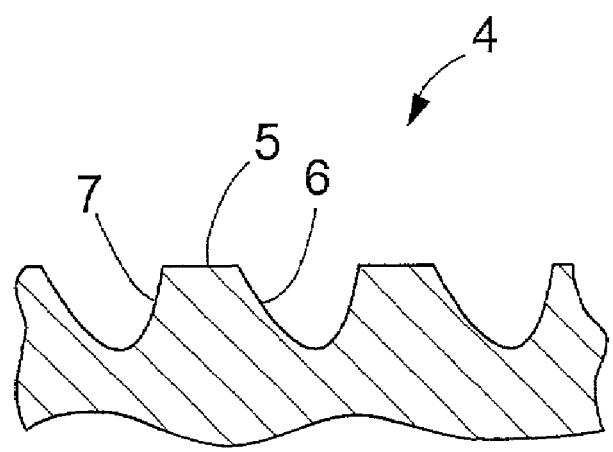
Figure 5:
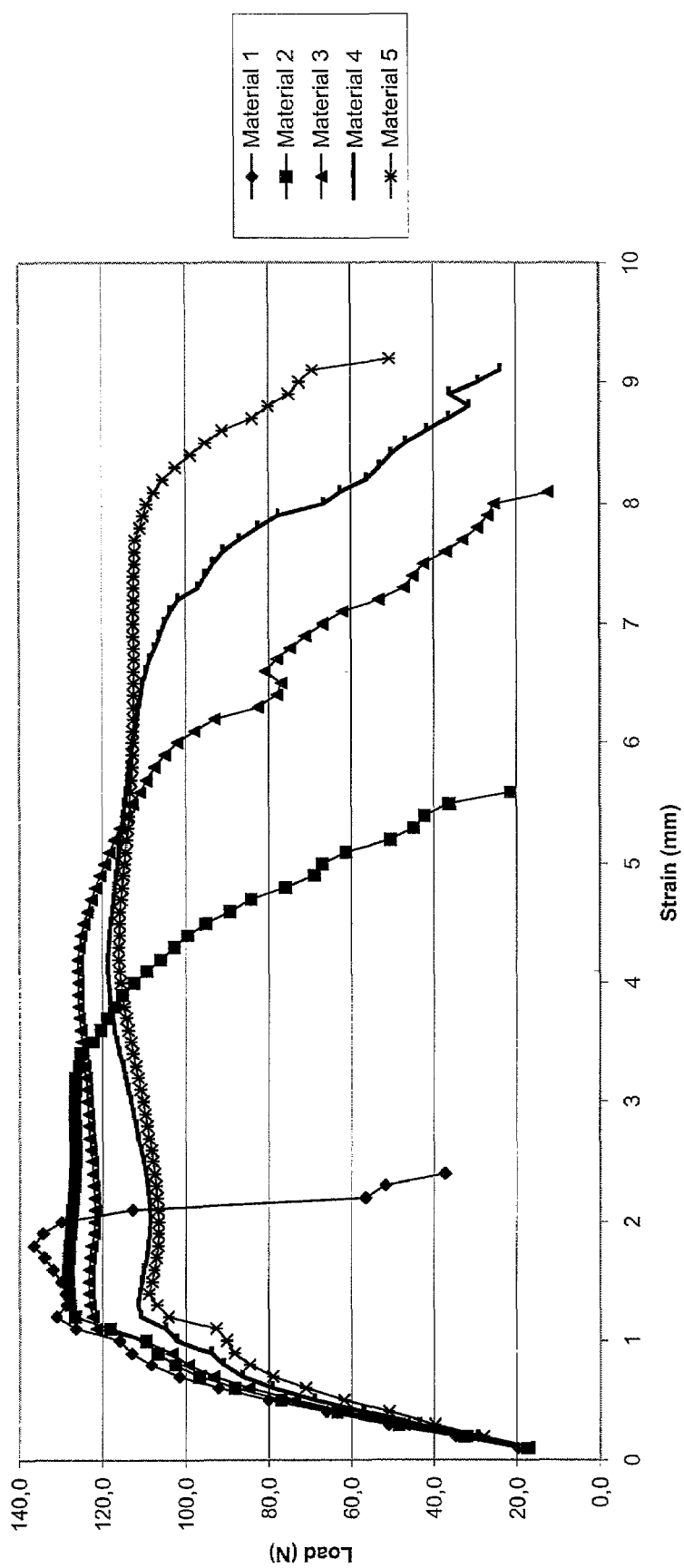

The invention will be described in greater detail in the accompanying drawings, in which FIG. 1 is a schematic side view of a fastening means according to the invention, FIG. 2 schematically illustrates the fastening means shown in FIG. 1 as seen from the head, FIG. 3 is a schematic cross-sectional view of the head of the fastening means shown in FIG. 1, FIG. 4 is a schematic cross-sectional view of the threaded section of a fastening means according to a second embodiment of the invention, and FIG. 5 schematically illustrates behaviour of materials according to the invention in a tensile strength test.

FIG. 1 is a schematic side view of a fastening means according to the invention. The fastening means comprises a head 1, which is provided with a contact portion for an installation tool. The fastening means further comprises an attaching part 3, which is provided with threads 4. The fastening means can be twisted into a threaded mounting hole in a manner known per se. It should be noted that the threaded mounting hole and its production are known per se to a person skilled in the art, for which reason these will not be described in greater detail in this application. The thread 4 is substantially symmetrical, i.e. the front side 6 and the back side 7 of the ridge 5 of the thread are at the same angle to the ridge 5. Such a thread is rather simple and economical to produce, as well as the tools needed to make the threaded mounting hole for the thread.

A special applicator is usually used for fastening a tack. The applicator pushes the tack into a mounting hole with a very quick movement; for this reason the method is called shooting. In shooting the tack, particularly its thread, is subjected to a considerable impact load in the axial direction. The thread 4 of the fastening means according to the invention is low. The height of the thread 4 is preferably at least 5% and at most 20% of the outer diameter D of the thread 4. The thread 4 has to have a certain minimum height to ensure sufficient tightness and fastening. On the other hand, the thread should not exceed a certain minimum height because this would reduce the strength of the thread and/or the stiffness of the fastening means too much. A particularly preferable height h for the thread is 8 to 12% of the outer diameter D of the thread 4. In that case the form factor of the thread 4 profile is very advantageous in respect of its strength. Thus the thread 4 and the fastening means sustain the load caused by shooting into the mounting hole very well. The fastening means of the invention is highly versatile because it can be used both as a screw and as a tack. Versatility simplifies and speeds up the surgeon's work because similar fastening means can be used for all fastening purposes the implant requires.

The fastening means is preferably made of a blend which contains a base material and one or more copolymer additives, which comprise one or more monomers so that the ductility of the blend at room temperature is higher than that of pure base material. These materials are described in greater detail in connection with FIG. 5 and Example 1.

FIG. 2 schematically illustrates the fastening means shown in FIG. 1 as seen from the head. The head 1 is provided with a contact portion for the installation tool. In the embodiment shown the contact portion consists of crossing perpendicular grooves 2 at the end, of the head 1. An installation tool similar to a crosshead screwdriver, for example, can be fitted into the grooves 2 for twisting the fastening means into the mounting hole. Naturally the installation tools used for pushing the fastening means into the mounting hole like a tack are also fitted into the contact portion. The turnable installation tool can be a manually used screwdriver, a motorized screw twister or a similar wrench known per se. The contact portion can also be some other driver member known per se, e.g. a hex socket, a hex head or the like.

The head 1 is provided with an attaching part, which in the embodiment of the invention shown in FIGS. 1 and 2 is a mounting cavity 8 at the intersection of the grooves 2 in the middle of the contact portion. At the end of the installation tool there is a corresponding mounting projection. It should be noted that the installation tools are not shown in the figures because they are known per se. The mounting cavity 8 is dimensioned so that the mounting projection of the installation tool is pressed into the mounting cavity 8, and thus the fastening means fastens detachably to the installation tool. In that case the fastening means stays firmly fastened to the tool regardless of its movements. After the fastening means has been placed in the mounting hole, the fastening tool is detached by pulling and/or twisting the mounting projection from the mounting cavity 8.

Fastening means of different sizes preferably have a mounting cavity 8 of the same size, and thus they all can be handled using the same installation tool. It should be noted that the attaching part may also differ from what has been described here.

FIG. 3 is a schematic cross-sectional view of the head of the fastening means shown in FIG. 1. The mounting cavity 8 of the fastening means is at the spot where the grooves 2 cross. The mounting cavity 8 of the installation tool extends to a distance from the bottom of the grooves 2. The mounting projection of the installation tool fastens firmly to the fastening means because the mounting cavity 8 is deep and the bevelled cutting edges 9 of the mounting cavity and the grooves 2 support the mounting projection over a long distance. The material of the fastening means also yields to some extent as the mounting projection of the installation tool is fitted into it, and the friction of the compressive force caused by the yield locks the fastening means into the tool.

FIG. 4 is a schematic cross-sectional view of a section of the thread of the fastening means according to an embodiment of the invention. The thread 4 is asymmetrical, i.e. the front side 6 of the ridge forms a substantially gentler angle with respect to the ridge 5 than the back side 7. This form reduces friction between the fastening means and the mounting hole when the fastening means is shot into the mounting hole in the direction of arrow P. However, the fastening force of the fastening means is sufficient in the opposite direction.

FIG. 5 schematically illustrates behaviour of materials according to the invention when loaded. The material is a blend, which contains a base material and one or more copolymer additives. The base material is a polymer or a copolymer of lactic acid, L-lactide, D-lactide, D,L-lactide, mesolactide, glycolic acid, glycolide or the like and optionally some other polymer or copolymer of a cyclic ester which is copolymerizable with lactide. The base material can also contain other co-monomers which impart desired properties to the material, such as $\alpha$, $\beta$ and $\gamma$-hydroxybutyric acid, $\alpha$, $\beta$ and $\gamma$-hydroxyvaleric acid and other hydroxy fatty acids ($C_{11}$ to $C_{25}$), such as stearic acid, palmitic acid, oleic acid, lauric acid and the like. Accordingly, the base material can be a polylactide, polyglycolide, poly(L-lactide), poly(D-lactide), poly(L-lactide-co-D,L-lactide), poly(L-lactide-co-mesolactide), poly(L-lactide-co-glycolide), poly(L-lactide-co-$\epsilon$-caprolactone), poly(D,L-lactide-co-mesolactide), poly(D,L-lactide-co-glycolide), poly(D,L-lactide-co-$\epsilon$-caprolactone), poly(mesolactide-co-glycolide), poly(mesolactide-co-$\epsilon$-caprolactone) or the like. The monomer units of the co-polymeric base material can be present in a ratio of 50:50 to 85:15 or in any other suitable ratio in between. For example, suitable co-polymeric base materials include poly(L-lactide-co-D,L-lactide) 70:30, poly(L-lactide-co-D,L-lactide) 80:20, poly(L-lactide-co-glycolide) 85:15 and poly(L-lactide-co-glycolide) 80:20. It should be noted that the polymers and copolymers suitable for use as the base material are-known per se and can be easily prepared by preparation methods which are well-known to a person skilled in the art.

The copolymer additive includes one or more of lactic acid, L-lactide, D-lactide, D,L-lactide, mesolactide, glycolic acid, glycolide or the like and one or more of trimethylene carbonate and dioxanone. Certain advantageous copolymer additives include poly(L-lactide-co-trimethylene carbonate), poly(D,L-lactide-co-trimethylene carbonate), poly(mesolactide-co-trimethylene carbonate), poly(glycole-co-trimethylene carbonate), poly(L-lactide-co-dioxanone), poly(D,L-lactide-co-dioxanone), poly(mesolactide-co-dioxanone), poly(glycolide-co-dioxanone) and the like.

EXAMPLE 1

Adding of copolymer additive to the base material yields a material with ductility better than that of pure base material. This is seen clearly in FIG. 5, which illustrates behaviour of five different materials in a tensile strength test.

The ratios of the main components included in the materials shown in FIG. 5 are given in Table 1.

TABLE 1

|  | P(L/LD)LA 70:30 (w-%) | PLLA/TMC 70:30 (w-%) |
| --- | --- | --- |
| Material 1 | 100 | 0 |
| Material 2 | 80 | 20 |
| Material 3 | 70 | 30 |
| Material 4 | 60 | 40 |
| Material 5 | 50 | 50 |

In Table 1 the abbreviation P(L/LD)LA 70:30 means poly(L-lactide-co-D,L-lactide) 70:30, and PLLA/TMC 70:30 means poly(L-lactide-co-trimethylene carbonate) 70:30. Material 1 is a prior art material into which no copolymer additive has been mixed. Materials 2 to 5 are embodiments of the material according to the invention and thus made of a blend which contains a base material and a copolymer additive, i.e. the base material is poly(L-lactide-co-D,L-lactide) 70:30 and the copolymer additive is poly(L-lactide-co-trimethylene carbonate) 70:30.

The test results shown in FIG. 5 were obtained in tests for which the test pieces were produced as follows: the blends were prepared from generally available components by dry mixing. A desired amount of components were mixed in a Turbula T2F mixer for 30 minutes to obtain a homogenous dry mixture. The dry mixture was dried in vacuum at 60° C. for 6 hours, after which it was melt-blended and injection moulded into test pieces.

A Fanuc Roboshot Alpha i30A injection moulding machine, in which the diameter of a screw with a standard profile was 16 mm, was used for producing a test piece. During the metering phase the counter pressure was 40 to 60 bar, the screw speed 60 to 100 $min^{-1}$ and the barrel temperature 160 to 230° C. In the injection phase the nozzle temperature was 180 to 230° C., the injection speed 80 to 300 mm/s, the maximum injection pressure 2500 bar and the pack pressure 1000 to 2300 bar for 3 to 8 seconds. The mould temperature was 20 to 30° C. and the cooling time 10 to 22 seconds. The cycle time of injection moulding was 20 to 40 seconds.

The tensile strength test was carried out as follows: a Zwick Z020/TH2A tensile testing machine and a load cell of 10 kN were used. The test was performed at room temperature. Gamma-sterilized test pieces were fixed to the jaws of the tensile testing machine immediately after the sterile package had been opened. Both jaws were provided with three tacks, which were fitted through the corresponding holes provided at both ends of the test piece. The test pieces were loaded at a constant speed of 5 mm/min until they broke.

As is seen in FIG. 5, material 1, i.e. the prior art material, behaves like a hard and brittle material typically does. In other words, its breaking strength is high but it has hardly any ductility. This material cannot be successfully used in the fastening means according to the invention because the probability that the material breaks when the fastening means is shot into a mounting hole like a tack is high. The reason for this is that the fastening means is subjected to a substantial impact load as it quickly penetrates into its mounting hole. Instead, materials 2 to 5, i.e. the materials according to the invention, have a substantially higher ductility than material 1, and thus they sustain the above-mentioned blow-like load substantially better than material 1. Materials 2 to 5 are consequently well suited for use as the material of the fastening means. It is also seen in FIG. 5 that the ductility of the material improves and the hardness decreases as the amount of copolymer additive increases. By choosing a suitable base material and copolymer additives and suitable ratios thereof, the hardness and ductility of the material can be adjusted rather freely. Materials 2 and 3 are particularly suitable for use as the raw material of the fastening means of the invention because they are ductile but hard.

It should be emphasized that substances other than the poly(L-lactide-co-D,L-lactide) 70:30 presented in Example 1 and in Table 2 can be used as the base material and substances other than the poly(L-lactide-co-trimethylene carbonate) can be used as the copolymer additive, as stated above in the application. The following combinations of base material and copolymer can be used in the production of the fastening means, for example:

poly(L-lactide-co-D,L-lactide) 80:20 and 20 to 40% by weight of poly(L-lactide-co-trimethylene carbonate) 70:30, poly(L-lactide-co-glycolide) 85:15 and 20 to 40% by weight of poly(L-lactide-trimethylene carbonate) 70:30, and poly(L-lactide-co-glycolide) 80:20 and 20 to 40% by weight of poly(L-lactide-co-trirmethylene carbonate) 70:30.

The drawings and the related description are only intended to illustrate the inventive concept. The details of the invention may vary within the scope of the claims. The fastening means can be shaped differently than the embodiments shown in the figures. Fastening means can be produced in different sizes. The material can contain about 50 to 99% of base material, i.e. the total amount of one or more copolymer additives is between 1 and 50% (by weight).

The invention claimed is:

1. A fastener for treatment of fractures, comprising a head having a contact portion for an installation tool, and an attaching part having a threaded portion, the threaded portion having a screw thread wherein the height of the screw thread is 5 to 20% of the outer diameter of the screw thread, wherein the fastener comprises a blend which contains a base material comprising a synthetic biodegradable polymer and at least one copolymer additive, which comprises one or more monomers, the blend being at room temperature substantially more ductile than pure base material.

2. A fastener according to claim 1, wherein the screw thread is substantially symmetrical.

3. A fastener according to claim 1, wherein the head is provided with an installation tool attaching part, which is arranged to fasten the installation tool detachably to the fastener.

4. A fastener according to claim 3, wherein the installation tool attaching part is a mounting cavity provided in the head.

5. A fastener according to claim 1, wherein the height of the screw thread is 8 to 12% of the outer diameter of the screw thread.

6. A fastener according to claim 1, wherein the copolymer additive contains trimethylene carbonate or dioxanone.

7. A fastener according to claim 6, wherein the copolymer additive is selected from the group consisting of poly(L-lactide-co-trimethylene carbonate), poly(D,L-lactide-co-trimethylene carbonate), poly(mesolactide-co-trimethylene carbonate), poly(glycolide-co-trimethylene carbonate), poly (L-lactide-co-dioxanone), poly(D,L-lactide-co-dioxanone), poly(mesolactide-co-dioxanone) and poly(glycolide-co-dioxanone).

8. A fastener according to claim 1, wherein the base material is selected from the group consisting of polylactide, polyglycolide, poly(L-lactide), poly(D-lactide), poly(L-lactide-co-D,L-lactide), poly(L-lactide-co-mesolactide), poly(L-lactide-co-glycolide), poly(L-lactide-co-ε-caprolactone) poly(D,L-lactide-co-mesolactide), poly(D,L-lactide-co-glycolide), poly(D,L-lactide-co-ε-caprolactone), poly(mesolactide-co-glycolide) and poly(mesolactide-co-ε-caprolactone).

9. A fastener according to claim 8, wherein the base material contains a copolymer selected from the group consisting of poly(L-lactide-co-D,L-lactide) 70:30, poly(L-lactide-co-D,L-lactide) 80:20, poly(L-lactide-co-glycolide) 85:15 and poly(L-lactide-co-glycolide) 80:20.

10. A fastener according to claim 1 comprising a blend which contains the base material, and one or more copolymer additives so that the ductility of the material mixture is at room temperature substantially higher than that of pure base material, wherein the share of the one or more copolymer additives in the blend is 1 to 20% by weight.

11. A fastener according to claim 1, wherein the base material is a copolymer in which the ratios of monomers range from 50:50 to 85:15.

12. A fastener according to claim 1, wherein the height of the screw thread is 5 to 12% of the outer diameter of the screw thread.

13. A fastener for treatment of fractures, comprising a head having a contact portion for an installation tool, and an attaching part having a threaded portion, the threaded portion having a screw thread wherein the height of the screw thread is 5 to 12% of the outer diameter of the screw thread, wherein the fastener comprises a blend which contains a base material comprising a synthetic biodegradable polymer and at least one copolymer additive, which comprises one or more monomers, the blend being at room temperature substantially more ductile than pure base material.

* * * * *